United States Patent
Pennell et al.

(10) Patent No.: US 10,436,703 B2
(45) Date of Patent: Oct. 8, 2019

(54) CYCLIC FLEXING SALT-SPRAY CHAMBER AND METHODS

(71) Applicant: THE BOEING COMPANY, Chicago, IL (US)

(72) Inventors: Sean M. Pennell, Huntsville, AL (US); Erik D. Sapper, St. Louis, MO (US); Andrew G. Wallburg, Madison, AL (US); Kristen S. Williams, Madison, AL (US)

(73) Assignee: THE BOEING COMPANY, Chicago, IL (US)

( * ) Notice: Subject to any disclaimer, the term of this patent is extended or adjusted under 35 U.S.C. 154(b) by 0 days.

(21) Appl. No.: 16/023,203

(22) Filed: Jun. 29, 2018

(65) Prior Publication Data
US 2018/0313745 A1 Nov. 1, 2018

Related U.S. Application Data

(63) Continuation of application No. 14/838,904, filed on Aug. 28, 2015, now Pat. No. 10,012,581.

(51) Int. Cl.
*G01N 17/02* (2006.01)
*G01N 17/00* (2006.01)
*G01N 3/32* (2006.01)

(52) U.S. Cl.
CPC ............ *G01N 17/02* (2013.01); *G01N 3/32* (2013.01); *G01N 17/002* (2013.01);
(Continued)

(58) Field of Classification Search
CPC ................................................. G01N 17/02
(Continued)

(56) References Cited

U.S. PATENT DOCUMENTS 3,226,965 A 1/1966 Higgins
4,096,742 A 6/1978 Musolf et al.
(Continued)

FOREIGN PATENT DOCUMENTS

CN 104977244 A 10/2015
DE 9309063 U1 8/1993
(Continued)

OTHER PUBLICATIONS

Standard Practice for Operating Salt Spray (Fog) Apparatus, ASTM International, Designation B117-11, Feb. 12, 2015, 12 pp.
(Continued)

*Primary Examiner* — Walter L Lindsay, Jr.
*Assistant Examiner* — Philipmarcus T Fadul
(74) *Attorney, Agent, or Firm* — Patterson + Sheridan, LLP (57) ABSTRACT

Aspects described herein generally relate to apparatus and methods for determining operational performance of material systems. Apparatus generally comprise a salt fog chamber having a fixture support having material system flexing components to test corrosion of an aircraft material system. In one aspect, a material performance chamber comprises a salt fog chamber and a jaw configured to flex a material system. Methods for determining corrosion include exposing a material system, such as a panel, to salt fog and flexing the material system at a frequency. In one aspect, a method for determining corrosion includes exposing a material system to a salt fog. The pH of the salt fog is from about 3.0 to about 9.0 and flexing the material system at a frequency from about 0.1 Hz to about 60 Hz.

19 Claims, 5 Drawing Sheets

(52) U.S. Cl.
CPC ... *G01N 17/006* (2013.01); *G01N 2203/0007* (2013.01); *G01N 2203/0023* (2013.01); *G01N 2203/024* (2013.01)

(58) Field of Classification Search
USPC .......................................................... 73/866
See application file for complete search history.

(56) References Cited

U.S. PATENT DOCUMENTS

| | | | |
|---|---|---|---|
| 5,188,456 A * | 2/1993 | Burke ..................... | G01N 3/08 374/50 |
| 6,615,671 B1 * | 9/2003 | Carstensen ............. | G01N 3/32 73/808 |
| 2010/0088788 A1 * | 4/2010 | Chasiotis ................ | G01N 19/04 850/33 |
| 2012/0052274 A1 | 3/2012 | Rehfeld et al. | |
| 2013/0011688 A1 * | 1/2013 | Beaver .................. | C25D 11/04 428/469 |
| 2014/0112822 A1 * | 4/2014 | Tanaka .................... | C22C 9/04 420/479 |

FOREIGN PATENT DOCUMENTS

| JP | S58-148340 A | 9/1983 |
|---|---|---|
| JP | S60-66133 A | 4/1985 |
| JP | H1116685 A | 1/1999 |
| JP | 2002536636 A | 10/2002 |
| JP | 2005-77220 A | 3/2005 |
| JP | 2012-242342 A | 12/2012 |
| JP | 2015-83929 A | 4/2015 |

OTHER PUBLICATIONS

Standard Practice for Modified Salt Spray (Fog) Testing, ASTM International, Designation G85-11, Feb. 12, 2015, 14 pp.
Zhang et al. Translation of CN104977244A. Published Oct. 2015. Translated Nov. 17, 2017.
Extended European Search Report for European Application No. 16183323.1 dated Dec. 19, 2016.
A.E.A. Chemin, Effect of Saline 1-15 Corrosion Environment on Fatigue Crack Growth of7475-T7351 Aluminum Alloy 2 ~nder Twist Flight Loading, Engineering Fracture Mechanics, vol. 141, May 27, 2015, pp. 274-290.
Non-Final Office Action dated Mar. 9, 2017 for U.S. Appl. No. 14/838,904.
Final Office Action dated Aug. 18, 2017 for U.S. Appl. No. 14/838,904.
Final Office Action dated Nov. 27, 2017 for U.S. Appl. No. 14/838,904.
Chinese Office Action for Applicaton No. 2017-205076 dated Aug. 27, 2018.

* cited by examiner

CYCLIC FLEXING SALT-SPRAY CHAMBER AND METHODS

CROSS-REFERENCE TO RELATED APPLICATIONS

This application is a continuation of U.S. patent application Ser. No. 14/838,904 filed Aug. 28, 2015, which is hereby incorporated by reference in its entirety.

FIELD

Aspects described herein generally relate to apparatus and methods for determining operational performance of material systems.

BACKGROUND

Spanning the lifetime of operation, an aircraft will experience repeated and harsh conditions resulting in degradation of component parts of the aircraft. Such degradation may take the form of, for example, corrosion and subsequent metal fatigue and fracture. Corrosion can contribute to a decrease in the integrity and strength of aircraft components. More specifically, a material system comprising aircraft components, such as fuselage or skin panels, a coated lap joint between two metal panels, or a wing-to-fuselage assembly on the exterior of an aircraft, may corrode over time due to exposure to mechanical and chemical stresses during use of the aircraft. Before a material is determined to be suitable for use as an aircraft material system, it may be desirable to determine the material system's propensity to corrode. However, performance of aircraft material systems, such as panels, during actual, real world use of the aircraft seldom correlates with corrosion testing data. Furthermore, corrosion tests often lack consistency between tests. For example, variability is observed when similar material systems are corroded in different testing apparatuses even though the testing conditions are nominally similar. Material system corrosion during actual use versus corrosion experienced during testing is particularly disparate when the material system comprises alloys or the material system has surface finishes, primers or top coats applied to the material system. Furthermore, conventional processes for testing corrosion are not effective at controlling the environment at any particular site on or within a test material system.

Therefore, there is a need in the art for methods and apparatus with controlled exposure environments for determining operational environment-specific performance, lifetime assessment, and failure mode investigation, i.e. an exposure environment that more closely mimics the conditions a material system will experience when incorporated as a component of an aircraft during actual, real-world use.

SUMMARY

Aspects described herein generally relate to methods and apparatus for determining operational environment-specific performance, lifetime assessment, and failure mode investigation of material systems.

In one aspect, a method for determining material performance includes exposing a material system to salt fog. The method further includes flexing the material system.

In another aspect, a method for determining material performance includes exposing a material system to a salt fog wherein the pH of the salt fog ranges from about 3.0 to about 9.0. The method further includes flexing the material system at a frequency from about 0.1 Hz to about 60 Hz.

In another aspect, a material performance chamber comprises a salt fog chamber and a jaw configured to flex a material system.

BRIEF DESCRIPTION OF THE DRAWINGS

So that the manner in which the above recited features of the present disclosure can be understood in detail, a more particular description of the disclosure, briefly summarized above, may be had by reference to aspects, some of which are illustrated in the appended drawings. It is to be noted, however, that the appended drawings illustrate only typical aspects of this present disclosure and are therefore not to be considered limiting of its scope, for the present disclosure may admit to other equally effective aspects.

Figure 5:
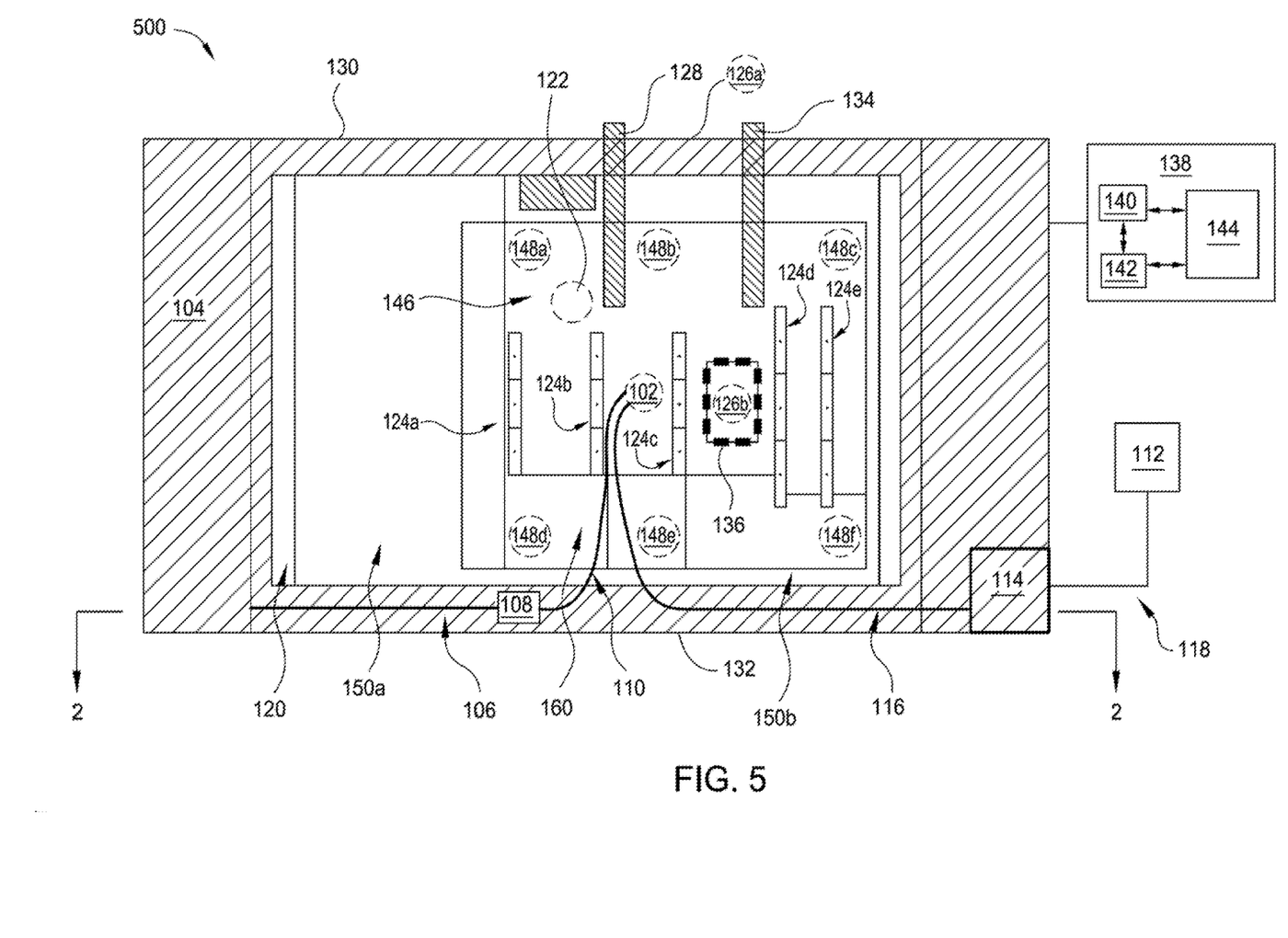
FIG. 5 is a plan view of an apparatus for accelerating and controlling the corrosion-related failure modes of a material system, according to an aspect of the disclosure.

To facilitate understanding, identical reference numerals have been used, where possible, to designate identical elements that are common to the figures. The figures are not drawn to scale and may be simplified for clarity. It is contemplated that elements and features of one aspect may be beneficially incorporated in other aspects without further recitation. For example, FIG. 5 is a plan view of an apparatus 500 for accelerating and controlling the corrosion-related failure modes of a material system, according to an aspect of the disclosure. As shown in FIG. 5, the components of apparatus 500 are the same as the components shown in apparatus 100 of FIG. 1, except that motor 126 is denoted as 126a and the apparatus includes a motor 126b coupled to first chamber wall 130.

DETAILED DESCRIPTION

The descriptions of the various aspects of the present disclosure have been presented for purposes of illustration, but are not intended to be exhaustive or limited to the aspects disclosed. Many modifications and variations will be apparent to those of ordinary skill in the art without departing from the scope and spirit of the described aspects. The terminology used herein was chosen to best explain the principles of the aspects, the practical application or technical improvement over technologies found in the marketplace, or to enable others of ordinary skill in the art to understand the aspects disclosed herein.

Aspects described herein generally relate to apparatus and methods for determining operational performance of material systems. For example, determining operational environment-specific performance, lifetime assessment, and failure mode investigation of material systems may be accomplished by aspects described herein. Apparatus generally comprise a salt fog chamber comprising material system flexing components to more accurately test corrosion of an aircraft material system such as a panel, a coated lap joint between two metal panels, and a wing-to-fuselage assembly. In one aspect, a corrosion chamber comprises an enclosure, a fog nozzle, a liquid reservoir, and a fixture support for gripping and flexing a material system. Methods for determining corrosion include exposing a material system to salt fog and flexing the material system at a frequency. In one aspect, a method for determining corrosion includes exposing a material system to a salt fog for a duration of about 1 hour to about 4500 hours wherein the pH of the salt fog is from about 3.0 to about 9.0 and flexing the panel at a frequency from about 0.1 Hz to about 60 Hz.

Figure 1:
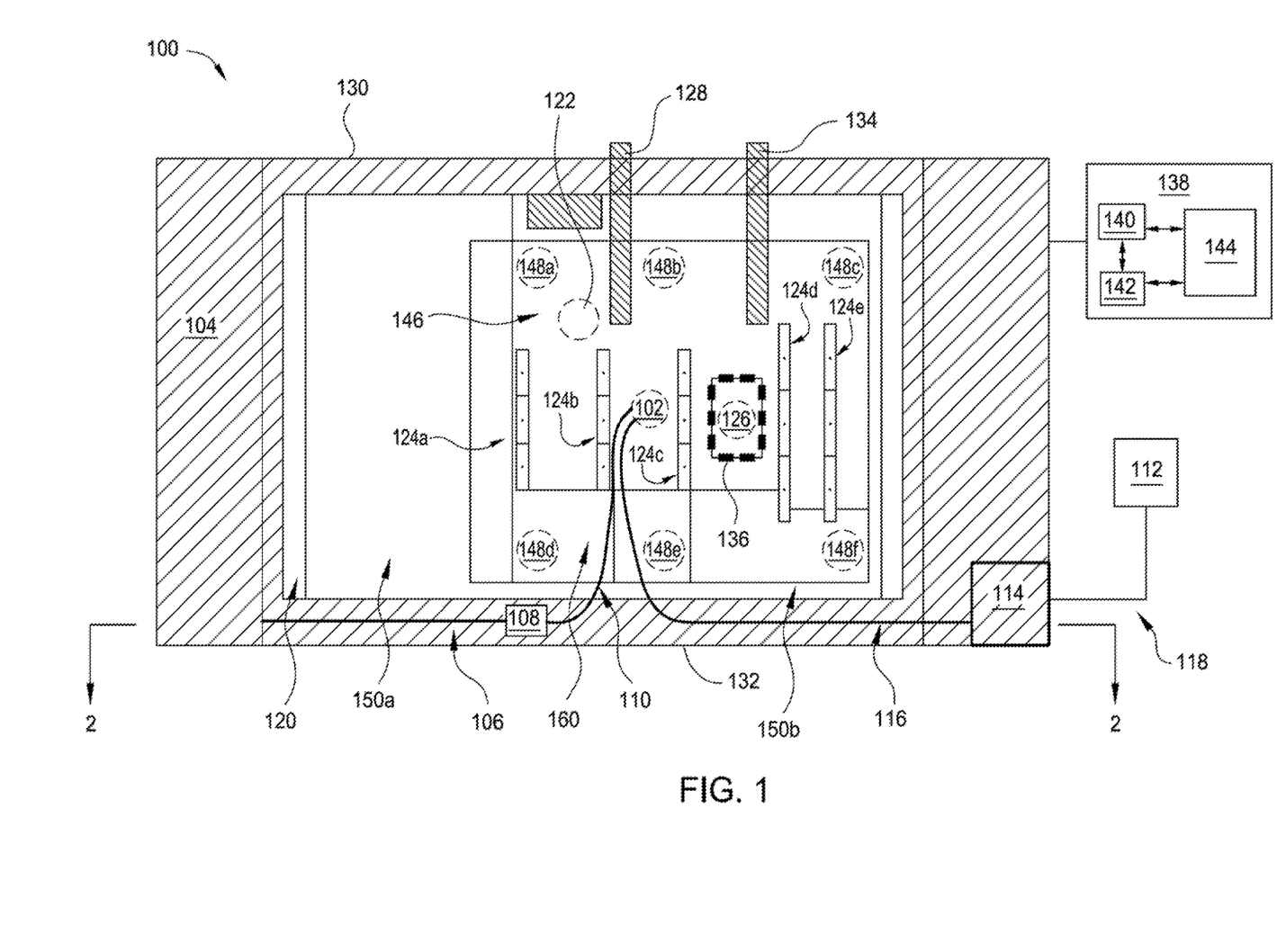
FIG. 1 is a plan view of an apparatus for accelerating and controlling the corrosion-related failure modes of a material system, according to an aspect of the disclosure.
Figure 2:
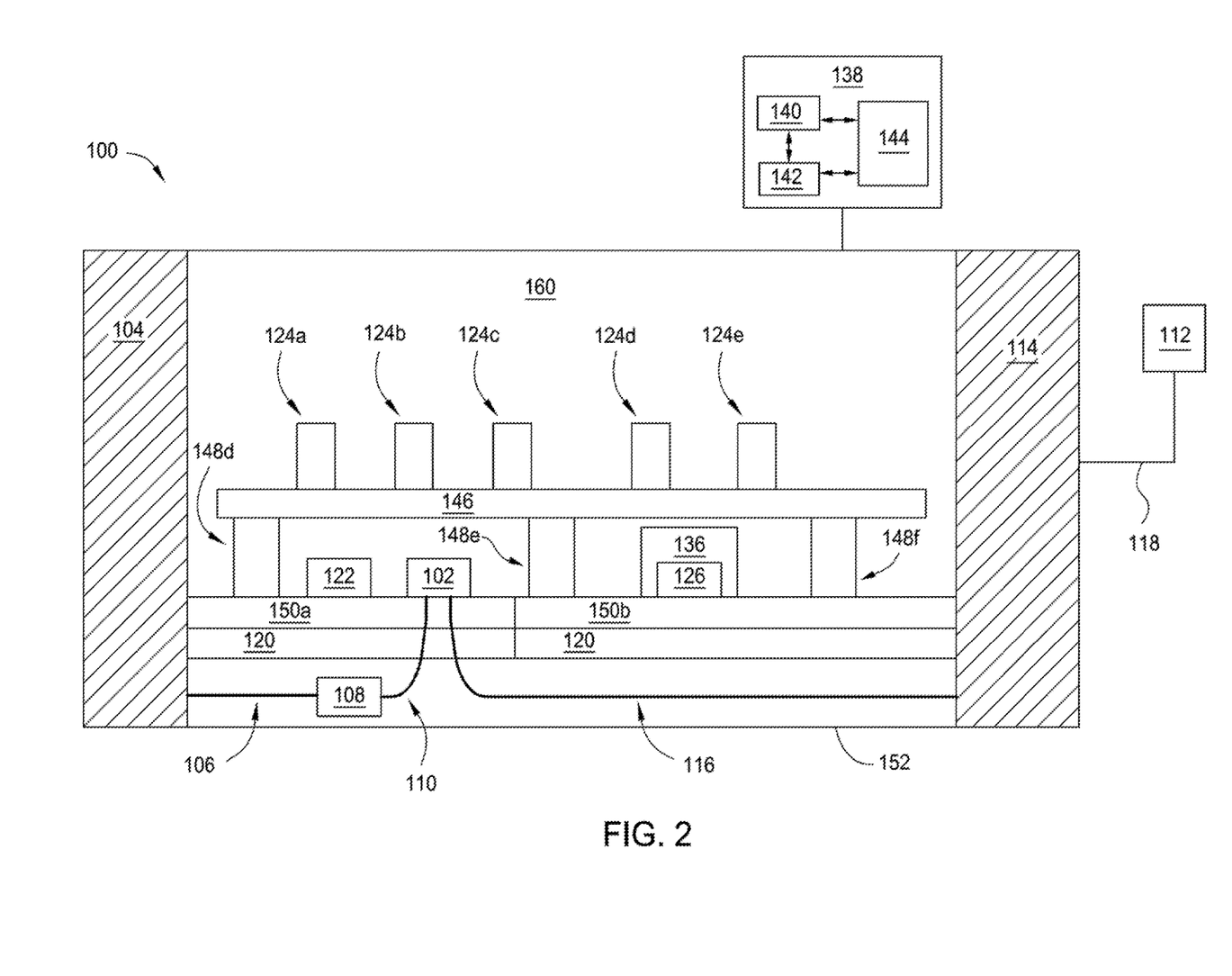
FIG. 2 is a side perspective view of an apparatus for accelerating and controlling the corrosion-related failure modes of a material system, according to an aspect of the disclosure.

FIG. 1 is a plan view of an apparatus 100 for accelerating and controlling the corrosion-related failure modes of a material system, according to an aspect of the disclosure. FIG. 2 is a side perspective view of apparatus 100 of FIG. 1. One or more components of apparatus 100 are made from materials that show resistance to a corrosive environment, such as an environment containing a salt fog. As shown in FIGS. 1 and 2, apparatus 100 includes an enclosure 160 having one or more fog nozzles 102 (one shown) disposed therein and configured to spray a treating liquid, such as a salt fog, in the enclosure 160. A fixture support is disposed in the enclosure to support a material system for exposure and flexing therein. Apparatus 100 includes a liquid reservoir 104 to supply a treating liquid to fog nozzle 102. Fog nozzle 102 may be a nozzle, such as an atomizing nozzle, a nozzle calibrated for air consumption, BETE full cone nozzle, hollow cone nozzle, fan misting nozzle, tank washing spray nozzle, NASA Mod1 nozzle for water spray atomization and droplet control, Q-Lab OEM fogging nozzle, Cool Clean ChilAire Lite spray applicator nozzle, and combinations thereof. Fog nozzle 102 may be comprised of materials such as hard rubber, plastic, or other inert materials.

The fixture support comprises jaws 124a-e configured to flex a material system. Plate 146 is configured to support jaws 124a-e. In some aspects, plate 146 comprises a mounting plate disposed on an I-Beam grate. Plate 146 is positioned between fog nozzle 102 and jaws 124a-124e (as shown in FIGS. 1 and 2), allowing treating liquid to enter the enclosure without directly impinging upon a material system held by one or more jaws 124a-e. This configuration mimics general humid atmospheric conditions, as compared to direct rainfall onto an aircraft material system. Alternatively, jaws 124a-e may be positioned between fog nozzle 102 and plate 146 (this configuration not shown), allowing direct flow of treating liquid toward a material system held by one or more jaws 124a-e. This configuration mimics direct rain fall or aerosol deposition onto an aircraft material system. Fog nozzle 102 may be configured for flow angle adjustment, allowing flow of treating liquid at one or more angles relative to a material system surface. In some aspects, a material system surface may be parallel to a principal direction of flow of liquid through apparatus 100, based upon the dominant surface being tested, which reduces liquid collection on a material system during corrosion testing performed in apparatus 100. In such aspects, fog nozzle 102 may be directed or baffled so that the liquid does not impinge directly on a material system. (Fog nozzle 102, a vent 122, a motor 126, an outer enclosure 136, and legs 148a-f are shown as dashed lines in FIG. 1 to indicate that these parts are located behind a plate 146 in the aspect shown in FIG. 1).

A fog pump 108 is configured to assist flow of a liquid from liquid reservoir 104 to fog nozzle 102 via first fluid line 106 and second fluid line 110. First fluid line 106 couples liquid reservoir 104 at a first end with fog pump 108 at a second end to provide liquid communication of liquid reservoir 104 with fog pump 108. Second fluid line 110 couples fog pump 108 at a first end with fog nozzle 102 at a second end to provide liquid communication of fog pump 108 with fog nozzle 102.

A compressed air source 112 and bubble tower 114 are configured to provide humidified air to fog nozzle 102. In some aspects, a pressure in the enclosure may be regulated to mimic the pressure experienced by an aircraft at various altitudes during real world use. Accordingly, compressed air source 112 is configured to flow air at a pressure ranging from about 2 PSI to about 50 PSI, from about 5 PSI to about 30 PSI, from about 12 PSI to about 18 PSI. In these ranges, lower pressure values mimic pressures experienced by an aircraft at higher altitudes while higher pressure values mimic pressures experienced by an aircraft at lower altitudes and closer to sea level. Air may include a mixture of gases similar to that found in an ambient atmosphere, for example, comprising about 78% $N_2$, about 21% $O_2$, and about 0.039% $CO_2$, among other gases. Third fluid line 116 couples bubble tower 114 at a first end with fog nozzle 102 at a second end to provide air and liquid communication of bubble tower 114 with fog nozzle 102. A compressed air line 118 couples compressed air source 112 at a first end with bubble tower 114 at a second end to provide air communication of compressed air source 112 with bubble tower 114. Bubble tower 114 may contain a liquid, such as water, to provide initial humidification or additional humidification to air flowed from compressed air source 112 via compressed air line 118.

A vent 122 may be coupled with the first chamber wall 130, a second chamber wall 132, or a third wall 152 (FIG. 2) to provide pressure regulation inside of apparatus 100. A heater 120 may be provided and configured to heat the inside of apparatus 100 such as enclosure 160. Heater 120 may be disposed adjacent to a first wall 130 of apparatus 100 and coupled with third wall 152 (FIG. 2). Heater 120 may be adhered to third wall 152 using by any suitable adherent, such as rivets. Heater 120 may be coupled with and controlled by controller 138.

Fixture support is configured to support and flex a material system positioned in the enclosure for testing. Jaws 124a, 124b, 124c, 124d, and 124e are configured to flex a material system, such as a panel, a coated lap joint between two metal panels, a wing-to-fuselage assembly, and combinations thereof. The material system may be an aircraft material system, such as a panel, such as a skin or fuselage flat panel. The material system may have a width that is, for example, about 4 inches, and a length that is for example, about 6 inches to about 14.5 inches. The fixture support may flex a material system to a strain ranging from about 0.05% to about 50%, about 0.1% to about 30%, about 0.3% to about 5%, such as about 0.37%.

Fixture support comprising one or more jaws 124a-e is configured to grip and release a material system. Jaws 124a-e are configured to flex a material system from a first starting position to a fully or partially flexed second position. Jaws 124a-e are configured to flex a material system from a first position to greater than 0° to about 180° from the starting position, such as about 5° to about 90°, such as about 5° to about 45°, during a flexing process. Jaws 124a-124e may be the same size or different sizes. For example, jaw 124a may be the same size as jaw 124b, but be a different size than jaw 124*d* (as shown in FIG. 1). Furthermore, jaws 124*a*-124*e* may be positioned from one another by a distance that is the same or different than a distance between a different pair of jaws 124*a-e*. For example, a first distance between jaw 124*a* and 124*b* may be different than a second distance between jaw 124*d* and 124*e*. Various jaw sizes and various distances between jaws allow, for example, simultaneous testing of different sized material systems, such as panels, during an exposing and flexing process within apparatus 100. In some aspects, one or more of jaws 124*a-e* comprises steel. In some aspects, one or more of jaws 124*a-e* is anodized. In some aspects, one or more of jaws 124*a-e* comprises an inert material such as hard rubber and/or plastic. In some aspects, jaws 124*a-e* are configured to support a material system, such as a panel, from about 15° and about 30° relative to a first wall 130 and/or second wall 132, which reduces liquid collection on a material system during corrosion testing performed in apparatus 100. In some aspects, jaw 124*a* is configured to grip a material system at a first end of the material system and jaw 124*b* is configured to grip the material system at a second end of the material system. In some aspects, jaws 124*a-e* are configured to flex a material system simultaneously or alternatively.

A motor 126 operates jaws 124*a-e*. Inlet tube 128 is coupled with motor 126 at a first end and coupled with first wall 130 at a second end for providing cooling material, such as air, to motor 126. Outlet tube 134 is coupled with motor 126 at a first end and coupled with first wall 130 at a second end for removing hot air exhaust from motor 126. Outer enclosure 136 surrounds motor 126 to enclose and protect the motor from liquid emitted from fog nozzle 102 or any other liquid present inside of apparatus 100. Jaws 124*a-e* are supported by plate 146. Plate 146 is supported by legs 148*a*, 148*b*, 148*c*, 148*d*, 148*e*, and 148*f*. Legs 148*a-f* are coupled with plate 146 at a first end and a chamber wall, a rack 150*a*, or a rack 150*b* at a second end. Parts of apparatus 100 described herein may comprise materials that are suitably inert to conditions within apparatus 100 during a cyclic flexing fog spray process. Suitably inert materials may include plastic, glass, stone, metal, rubber, and/or epoxy.

Apparatus 100 may be controlled by a processor based system controller such as controller 138. For example, the controller 138 may be configured to control apparatus 100 parts and processing parameters associated with a cyclic flexing fog spray process. The controller 138 includes a programmable central processing unit (CPU) 140 that is operable with a memory 142 and a mass storage device, an input control unit, and a display unit (not shown), such as power supplies, clocks, cache, input/output (I/O) circuits, and the like, coupled to the various components of the apparatus 100 to facilitate control of a cyclic flexing fog spray process. Controller 138 may be in electronic communication with, for example, outlet tube 134, vent 122, heater 120, and/or jaws 124*a-e*.

To facilitate control of the apparatus 100 described above, the CPU 140 may be one of any form of general purpose computer processor that can be used in an industrial setting, such as a programmable logic controller (PLC), for controlling various chambers and sub-processors. The memory 142 is coupled to the CPU 140 and the memory 142 is non-transitory and may be one or more of readily available memory such as random access memory (RAM), read only memory (ROM), floppy disk drive, hard disk, or any other form of digital storage, local or remote. Support circuits 144 are coupled to the CPU 140 for supporting the processor in a conventional manner. Information obtained from cyclic flexing fog spray processes with apparatus 100 may be stored in the memory 142, typically as a software routine. The software routine may also be stored and/or executed by a second CPU (not shown) that is remotely located from the hardware being controlled by the CPU 140. The memory 142 is in the form of computer-readable storage media that contains instructions, that when executed by the CPU 140, facilitates the operation of the apparatus 100. The instructions in the memory 142 are in the form of a program product such as a program that implements the method of the present disclosure. The program code may conform to any one of a number of different programming languages. In some aspects, the disclosure may be implemented as a program product stored on computer-readable storage media for use with a computer system. The program(s) of the program product define functions of the aspects (including the methods described herein). Illustrative computer-readable storage media include, but are not limited to: (i) non-writable storage media (e.g., read-only memory devices within a computer such as CD-ROM disks readable by a CD-ROM drive, flash memory, ROM chips or any type of solid-state non-volatile semiconductor memory) on which information is permanently stored; and (ii) writable storage media (e.g., floppy disks within a diskette drive or hard-disk drive or any type of solid-state random-access semiconductor memory) on which alterable information is stored. Such computer-readable storage media, when carrying computer-readable instructions that direct the functions of the methods and apparatus described herein, are aspects of the present disclosure.

Figure 3:
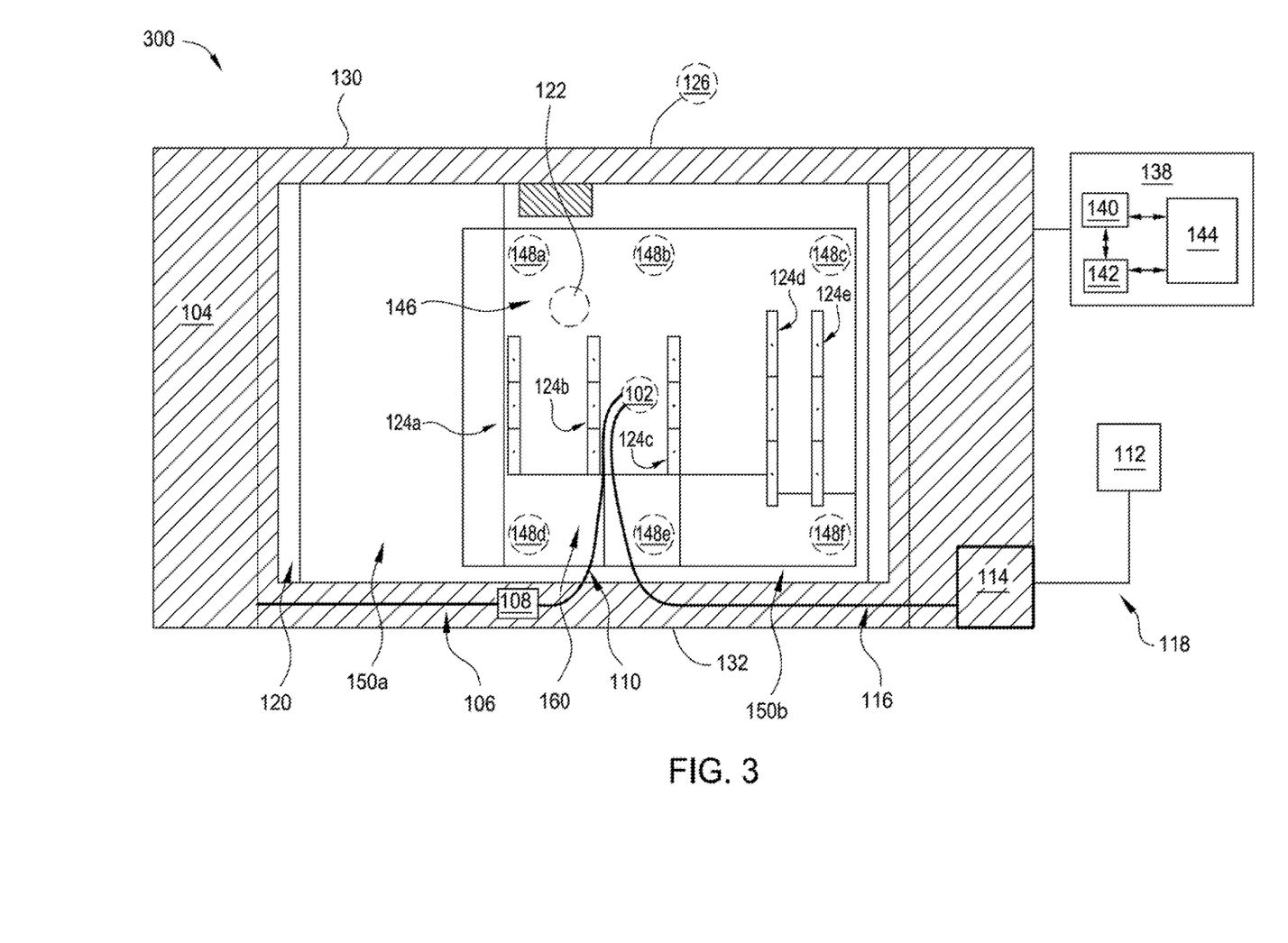
FIG. 3 is a plan view of an apparatus for accelerating and controlling the corrosion-related failure modes of a material system, according to an aspect of the disclosure.

FIG. 3 is a plan view of an apparatus 300 for accelerating and controlling the corrosion-related failure modes of a material system, according to an aspect of the disclosure. As shown in FIG. 3, the components of apparatus 300 are the same as the components shown in apparatus 100 of FIG. 1, except that motor 126 is not encompassed by outer enclosure 136 (outer enclosure 136 is not present), motor 126 is located external to first chamber wall 130, and inlet tube 128, and outlet tube 134 are not present. Motor 126 is coupled to first chamber wall 130. In some aspects, motor 126 (coupled to first chamber wall 130) translates bending motion inside the chamber via a screw, such as a ball screw, Acme screws, Lead screws, Roller screws, and screw mount, or an axle, passing into the chamber (not shown). A screw maintains spacing between stationary block 406 and mobile block 404 during flexing.

Figure 4:
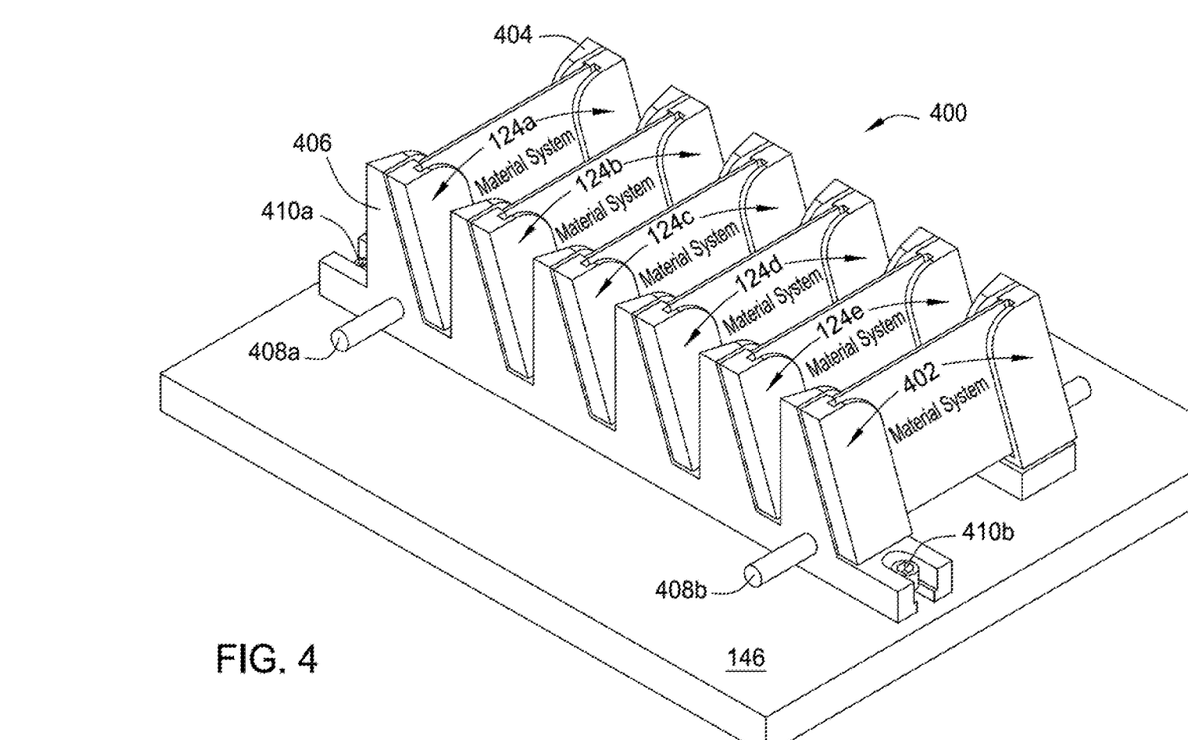
FIG. 4 is a perspective view of a flexer configured to perform cyclic flexing, according to an aspect of the disclosure.

FIG. 4 is a perspective view of a flexer 400 configured to perform cyclic flexing, according to an aspect of the disclosure. Flexer 400 may be located inside of a material performance chamber, as described for FIG. 1. As shown in FIG. 4, flexer 400 includes a mobile block 404 and a stationary block 406. Stationary block 406 is mounted to plate 146 by mounting bolts 410*a* and 410*b*. Mobile block 404 is slidably disposed on plate 146 adjacent to stationary block 406. Linear displacement between stationary block 406 and mobile block 404 is maintained by guide rods 408*a* and 408*b*. Guide rods 408*a* and 408*b* may comprise stainless steel, high density polypropylene, high density polyethylene, chromium, such as an Armology coating, and combinations thereof. Each of guide rods 408*a* and 408*b* is coupled with stationary block 406 and mobile block 404. Guide rods 408*a* and 408*b* are parallel to one another. Stationary block 406 and mobile block 404 mount or otherwise support jaws 124*a-f*. Stationary block 406 mounts a first side of jaws 124*a-f* in a stationary position during flexing, while mobile block 404 mounts a second side of jaws 124*a-f* and allows movement of the second side of jaws

124*a-f* during flexing. Stationary block 406 and mobile block 404 may comprise high density polyethylene. During flexing, the mobile block is shifted laterally relative to the stationary block from a starting point to an end point resulting in flexing of the material system positioned in jaws 124*a-f*. The starting point, end point, and shift distance may be controlled by a user of flexer 400 based on test fixture mechanical boundary limits, mechanical stop blocks, or fixture driving system software controls. Each of stationary block 406 and mobile block 404 includes a base and a plurality of stanchions extending from the base perpendicular thereto. Each stanchion may be rectangular or angled to provide an angle on which each of the jaws 124*a-f* can be mounted. Jaws 124*a-f* are hinged, which allows bending of a material system while compressing the material system. For example, jaws 124*a-f* may be mounted on one side of each stanchion and disposed at an angle from, for example, 15° to 30° relative to a line perpendicular to the base. Other angles relative to perpendicular are contemplated to achieve a desired testing condition for a material panel. The angle of jaws 124*a-f* determines the angular position of the material system. In some aspects, a material system is disposed at an angle from, for example, 15° to 30° relative to a line perpendicular to the base. In some aspects, jaws 124*a-f* are non-conductive and non-metallic so as to have little or no galvanic effect on the material system. One or more of jaws 124*a-f* may comprise high density polyethylene, commercial grade Titanium (II) with polyethylene insert, sacrificial 316 stainless steel (316SS) with polyethylene insert, or combinations thereof, which prevents (partially or completely) galvanic corrosion of the jaws and material systems during testing. One or more of jaws 124*a-f* may comprise a sleeve cover comprising, for example, polyethylene, which further prevents galvanic corrosion of the jaws and material systems during testing. In some aspects of the present disclosure, a material performance chamber contains more than one flexer 400. In some aspects where a material performance chamber contains more than one flexer 400, guide rods 408*a* and 408*b* extend through multiple flexers 400.

A flexer, such as flexer 400, provides variable displacement of a mobile block and material systems at variable frequencies that are adjustable in real-time. A flexer also allows for application of tension and compression to a material system.

A material testing process such as a cyclic flexing fog spray process, for example, within apparatus 100, may be performed by exposing a material system, such as a panel, to a treating liquid, such as a salt fog, and flexing the material system. The exposing may be performed for from about 1 hour to about 4500 hours, such as about 200 hours to about 2000 hours, such as about 500 hours to about 1000 hours. Exposing a material system to a treating liquid for about 1 hour mimics, for example, salt fog exposure experienced by the material system as part of an aircraft in an arid climate. Exposing a material system to a treating liquid for about 4500 hours mimics, for example, salt fog exposure experienced by the material system as part of an aircraft in a very humid climate or a moderately humid climate for a prolonged period of time. The liquid may contain water that is reagent grade water. The liquid may be a salt solution. The salt solution may comprise sodium chloride. The salt solution may contain about 2 parts sodium chloride in 98 parts water to about 6 parts sodium chloride in 94 parts water, such as about 5 parts sodium chloride in about 95 parts water. The liquid, such as a salt solution, may contain less than about 0.1% of bromide, fluoride and iodide. The liquid, such as a salt solution, may contain less than about 1 ppm, such as about 0.3 ppm, by mass of copper. The liquid, such as a salt solution, might not contain anti-caking agents, as such agents may act as corrosion inhibitors. Material systems which may be tested include, for example, aircraft panels which may form the skins or fuselage of an aircraft, a coated lap joint between two metal panels, a wing-to-fuselage assembly, and combinations thereof. The material systems may comprise a metal or alloy. Common material systems may comprise aluminum. Panels may comprise aluminum and/or an alloy, such as AA2024, AA7075, AA5083, aluminum lithium, or high entropy multicomponent alloys. The liquid may be atomized to form the treating liquid, such as a salt fog, that may have a pH ranging from about 3 to about 11, such as about 5 to about 8, such as about 6.5 to about 7.2. pH may be measured using a suitable glass pH-sensing electrode, reference electrode, and pH meter system. It may be desirable to adjust the pH of the treating liquid. For example, a treating liquid having a low pH may mimic a polluted atmosphere containing acid rain and the like. Furthermore, pH of the liquid that is atomized into the treating liquid may be adjusted to recalibrate the liquid during an exposing process. pH may be adjusted by, for example, addition of hydrochloric acid (HCl) to decrease the pH or addition of sodium hydroxide (NaOH) to increase the pH. The liquid, such as a salt fog, may be flowed at a rate of about 0.5 milliliters per hour (mL/h) to about 5 mL/h per 80 cm$^2$ of horizontal collection area, such as about 1 mL/h to about 2 mL/h per 80 cm$^2$ of horizontal collection area. In some aspects, a material system, such as a panel, may be flexed by a fixture support using one of jaws 124*a-e* or by a plurality of jaws 124*a-e*. Flexing may be performed at varying frequencies to mimic the effect of mechanical stresses for corrosive conditions experienced by an aircraft material system under real world conditions. For example, a material system may be flexed at a frequency from about 0.1 Hertz (Hz) to about 150 Hz, about 0.1 Hz to about 100 Hz, about 0.1 Hz to about 60 Hz. Furthermore, the greater the curvature of a flexed material system, the greater the degradation to the material system using apparatus and methods of the present disclosure. For example, a flat panel having a length of 6 inches may be gripped by two jaws with a distance of 6 inches between the two jaws. The panel may be flexed at a rate of 0.33 Hz during exposure to a salt fog solution. In another example, a flat panel having a length of 7.5 inches may be gripped by two jaws also having a distance of 6 inches between the two jaws. The panel may be flexed at a rate of 0.33 Hz during exposure to a salt fog solution. The panel having a length of 7.5 inches has an increased curvature and undergoes increased degradation as compared to the panel having a length of 6 inches under otherwise identical conditions. Without being bound by theory, mechanical stresses that give curvature to a material system result in cracking of the material system which permits access of corrosive fluid, such as a salt fog, into a crack of the material system. After entering a crack of the material system, corrosive fluid may further enter between various additional layers, if present, on the surface of the material system. Additional layers may include, for example, a surface finish, a primer, and/or a top coat. Accordingly, corrosive fluid may cause corrosion of the material system and/or one or more of the additional layers of the material system. Such conditions mimic the conditions experienced by an aircraft material system, such as a panel, during real world use.

In some aspects, an exposure zone, such as an enclosure 160 of apparatus 100, may be maintained at a temperature ranging from about −196° C. to about 100° C., −50° C. to about 95° C., 0° C. to about 50° C., such as about 33° C. to about 37° C., for example about 35° C., during the exposing of a material system to a treating liquid (such as a salt solution atomized into a salt fog), and/or the flexing the material system. The temperature may be monitored by a recording device or by a thermometer (not shown) that can be read from an outside surface of apparatus 100. In some aspects, exposing a material system, such as a panel, to a liquid, such as a salt fog, and flexing the material system may be performed concurrently. In some aspects, exposing a material system, such as a panel, to a liquid, such as a salt fog, and flexing the material system may be performed sequentially. In some aspects, a material system may be exposed to a salt fog and flexed concurrently as well as sequentially, which provides recreation of an irregular or variable flight-specific strain profile that may be experienced by a material system in service. In some aspects, exposing a material system to a liquid and/or flexing the material system may be interrupted to inspect, rearrange, or remove the material system, and/or replenish a solution, such as a solution in liquid reservoir 104.

Once the exposing process is complete, the extent of corrosion is measured. The material system is washed, such as with water, to remove byproducts of the treating solution, e.g., salt deposits, from the surface of the material system, followed by drying of the material system. A material system may, additionally or alternatively, be washed with an HCl solution and/or hexamethylene tetramine, followed by rinsing with reagent grade water. After washing, the material system may be dried. The extent of corrosion may be determined by a mass loss technique by weighing the material system after washing/drying and subtracting the weight from the weight of the material system before the exposing to a liquid, such as a salt fog, and the flexing.

A material system, such as a panel, may have one or more surface layers such as a surface finish, a primer, and/or a top coat. Corrosion may occur at one or more of these layers in a real world setting due to mechanical and chemical stresses. Apparatus and methods described herein allow for corrosion testing that mimics the corrosion experienced by a material system under real world conditions by subjecting the material system to mechanical as well as chemical stresses. Apparatus and methods described herein allow for corrosion testing at one or more of a material system surface, a finished surface, a primer surface, and/or a top coat surface.

EXAMPLE 1

An aluminum panel measuring 3.75 inches wide by 14.5 inches long was secured by two jaws in a fixture support in the device described in FIG. 1. While flexing the panel at about 1 Hz, the panel was exposed to a sodium chloride salt fog (pH 6.8) for 500 hours. After the exposing and flexing, the aluminum panel was washed with water and dried. To determine the overall corrosion of the panel under these conditions, the panel was then weighed, and this weight was subtracted from the weight of the panel prior to exposing and flexing. Further, electrochemical measurements were made on the material system to assess degree and extent of corrosive damage imparted during the test.

In some aspects, a material system is a flat metal panel, which may be coated. The material performance of the flat panel is tested by cyclically flexing the panel while exposing the panel to at least a cycle of salt fog. Following exposure and flexing, the panel is assessed for corrosion onset, rate of propagation, and performance.

In some aspects, a material system comprises two flat metal panels connected, joined, or fastened together using metallic fasteners, screws, bolts, or other hardware, before being exposed to at least a cycle of salt fog. The material system may then be assessed for corrosion onset, rate of propagation, and performance.

In some aspects, a material system comprises a mechanical joint or knuckle joint that may be made of metallic or composite materials and coated before being exposed to a cyclic salt fog before being assessed for corrosion onset, rate of propagation, and performance.

In some aspects, a material system comprises a structural system replicative of aircraft components, representing a side-of-body join, a stringer-to-fuselage assembly, a fuselage panel, or wing spar-to-fuselage assembly. The produced assemblies may be actuated or flexed while being exposed to at least a cycles of salt fog before being assessed for corrosion onset, rate of propagation, and performance.

Apparatus and methods described herein provide a controlled salt fog environment and monitoring of material performance, such as corrosion, on a variety of material systems, such as aircraft material systems, such as panels, coated lap joints between two or more panels, wing-to-fuselage assemblies, and combinations thereof. Apparatus and methods described herein provide an ability to replicate in-service, real-world failure modes and mechanisms in a controlled exposure environment.

Mechanical flexing of a material system in an apparatus of the present disclosure may result in increased corrosion of a material system, such as a panel. The compounding effects of mechanical and chemical stresses combine to induce corrosion, which more accurately replicates corrosion experienced by a material system, such as an aircraft panel, in a real-world environment. Accordingly, the methods and apparatus of the present disclosure more accurately simulate the corrosion observed with aircraft material systems during real-world use of the aircraft. Methods and apparatus of the present disclosure allow for testing corrosion of stand-alone material systems and the interfaces between coating layers, which more accurately represents the corrosion experienced by material systems, such as panels, during actual use of the material systems as part of an aircraft. The methods and apparatus of the present disclosure further allow re-creation of irregular flight-specific strain profiles so that improved predictive as well as forensic investigations of aircraft material systems may be performed.

While the foregoing is directed to aspects of the present disclosure, other and further aspects of the present disclosure may be devised without departing from the basic scope thereof. Furthermore, while the foregoing is directed to material systems, such as aircraft material systems, such as panels, coated lap joints between two or more panels, and wing-to-fuselage assemblies, aspects of the present disclosure may be directed to other material systems not associated with an aircraft, such as a multicomponent material system used in aerospace, automotive, marine, energy industry, and the like.

What is claimed is:

1. A method for determining material performance comprising:
    exposing a material panel to a salt fog wherein the pH of the salt fog ranges from about 3.0 to about 9.0; and
    flexing the material panel at a frequency from about 0.1 Hz to about 60 Hz,
    wherein the exposing the material panel and the flexing the material panel are performed concurrently in the same chamber.

2. The method of claim 1, wherein the flexing is performed by a jaw coupled with the material panel and a motor coupled with the jaw.

3. The method of claim 1, further comprising maintaining an exposure zone at a temperature of from about −50° C. to about 95° C. during the exposing the material panel to salt fog.

4. The method of claim 1, wherein the flexing the material panel comprises bending the material panel.

5. A material performance chamber comprising:
a salt fog chamber;
a jaw configured to flex a material system;
a mobile block and a stationary block;
a first guide rod coupled at a first end with the mobile block and coupled at a second end with the stationary block; and
a second guide rod coupled at a first end with the mobile block and coupled at a second end with the stationary block.

6. The material performance chamber of claim 5, further comprising a motor located external to the chamber.

7. The material performance chamber of claim 5, wherein the motor comprises an outer enclosure.

8. The material performance chamber of claim 5, further comprising:
a controller in electrical communication with a vent, a heater, and the jaw.

9. The material performance chamber of claim 5, wherein the jaw comprises a material selected from the group consisting of high density polyethylene, high density polypropylene, commercial grade Titanium (II) with polyethylene insert, stainless steel with polyethylene insert, and combinations thereof.

10. The material performance chamber of claim 5, wherein the jaw comprises a sleeve cover, wherein the sleeve cover comprises polyethylene.

11. The material performance chamber of claim 5, wherein the jaw is non-conductive and non-metallic.

12. The material performance chamber of claim 5, wherein the stationary block and the mobile block comprise a base and a plurality of stanchions extending from the base.

13. The material performance chamber of claim 5, wherein the jaw is disposed on the mobile block at a first end and disposed on the stationary block at a second end.

14. A material performance chamber comprising:
a salt fog chamber;
a plate;
a flexer disposed on the plate and comprising:
a plurality of jaws configured to flex one or more material systems,
a first block and a second block disposed on the plate, wherein the first block is mounted to the plate,
a first rod coupled at a first end with the first block and coupled at a second end with the second block, and
a second rod coupled at a first end with the first block and coupled at a second end with the second block.

15. The material performance chamber of claim 14, wherein the first block and the second block comprise a base and a plurality of stanchions extending from the base.

16. The material performance chamber of claim 14, wherein at least one jaw of the plurality of jaws is configured to dispose a material system of the one or more material systems at an angular position.

17. The material performance chamber of claim 14, further comprising a fog nozzle, a compressed air source and a tower configured to provide humidified air to the fog nozzle.

18. The material performance chamber of claim 14, wherein the jaws of the plurality of jaws are disposed on the first block at a first end and disposed on the second block at a second end.

19. The material performance chamber of claim 14, wherein the jaws of the plurality of jaws comprise a material selected from the group consisting of high density polyethylene, high density polypropylene, commercial grade Titanium (II) with polyethylene insert, stainless steel with polyethylene insert, and combinations thereof.

* * * * *